United States Patent [19]

Bouzard et al.

[11] 4,091,215

[45] May 23, 1978

[54] 7-D-α-AMINO-α-(P-ACETOXYPHENYL)-ACETAMIDO-3-METHYL-3-CEPHEM-4-CARBOXYLIC ACID

[75] Inventors: Daniel Bouzard, Franconville; Abraham Weber, Paris, both of France

[73] Assignee: Bristol-Myers Company, New York, N.Y.

[21] Appl. No.: 770,876

[22] Filed: Feb. 22, 1977

Related U.S. Application Data

[62] Division of Ser. No. 581,054, May 27, 1975, Pat. No. 4,012,382.

[30] Foreign Application Priority Data

Jun. 5, 1974 United Kingdom ............... 24848/74

[51] Int. Cl.² .......................................... C07D 501/22
[52] U.S. Cl. ..................................................... 544/30
[58] Field of Search ......................................... 544/30

[56] References Cited

U.S. PATENT DOCUMENTS

| 3,655,656 | 4/1972 | Van Heyningen | 260/243 C |
|---|---|---|---|
| 3,668,203 | 6/1972 | Clark et al. | 424/246 |
| 3,855,213 | 12/1974 | Dunn et al. | 544/30 |
| 4,018,921 | 4/1977 | Gleason | 544/30 |

*Primary Examiner*—Donald G. Daus
*Assistant Examiner*—David E. Wheeler
*Attorney, Agent, or Firm*—Herbert W. Taylor, Jr.

[57] ABSTRACT

7-D-α-Amino-α-(p-acetoxyphenyl)acetamido-3-methyl-3-cephem-4-carboxylic acid is prepared in a form substantially free of the L-isomer and hydrolyzed enzymatically, preferably using wheat bran, to produce p-hydroxycephalexin (cefadroxil).

1 Claim, No Drawings

7-D-α-AMINO-α-(P-ACETOXYPHENYL) ACETAMIDO-3-METHYL-3-CEPHEM-4-CARBOXYLIC ACID

CROSS-REFERENCE TO RELATED APPLICATION

This application is a division of our prior, copending application Ser. No. 581,054 filed May 27, 1975 and issued Mar. 15, 1977 as U.S. Pat. No. 4,012,382.

BACKGROUND OF THE INVENTION

1. Field of the Invention

This invention relates to the production and use of chemicals of the cephalosporin class which are particularly useful in the treatment of bacterial infections by oral administration.

2. Description of the Prior Art p-Hydroxycephalexin, now known as cefadroxil, was disclosed, inter alia, in U.S. Pat. Nos. 3,489,752 and 3,985,741.

Generic formulae which include alkanoyloxy substituents on the benzene ring of α-amino-7-phenylacetamidodesacetoxycephalosporanic acid are found in numerous patents, e.g. U.S. Pat. No. 3,579,514. The cephalexin art has been reviewed, for example, in U.S. Pat. Nos. 3,985,741, 3,579,514 and 3,843,639.

Enzymatic cleavage has frequently been used to remove the acetyl group from cephalosporins containing a 3-acetoxymethyl substituent as in U.S. Pat. Nos. 3,532,694, 3,436,310 and 3,202,656.

SUMMARY OF THE INVENTION

The novel cephalosporin derivative of this invention is the D- compound of the formula

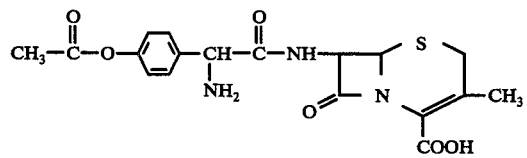

and pharmaceutically acceptacle salts thereof when substantially free of the L- isomer.

The pharmaceutically acceptacle salts referred to above include the nontoxic carboxylic acid salts, e.g. nontoxic metallic salts such as sodium, potassium, calcium and alumnium, the ammonium salt and salts with nontoxic amines, e.g. trialkylamines, procaine, dibenzylamine, N-benzyl-β-phenethylamine, 1-ephenamine, N,N'-dibenzylethylenediamine, N-alkylpiperidine and other amines which are used to form salts of penicillins and cephalosporins. Also included within the definition of pharmaceutically acceptable salts are the nontoxic acid addition salts (amine salts), e.g. salts with mineral acids such as hydrochloric, hydrobromic, hydroiodic, phosphoric, sulfuric and salts with organic acids such as maleic, acetic, citric, oxalic, succinic, benzoic, tartaric, fumaric, mandelic, ascorbic and malic.

The pharmaceutically active compounds of the present invention are potent antibacterial agents useful in the treatment of infectious diseases in poultry and animals, including man, caused by many Gram-positive and Gram-negative bacteria. The active compounds are also of value as nutritional supplements in animal feeds and as agents for the treatment of mastitis in cattle. The preferred compounds have also been unexpectedly found to be efficiently absorbed upon oral administration.

The novel medicaments provided by the present invention may be formulated as pharmaceutical compositions comprising, in addition to the active ingredient, a pharmaceutically acceptable carrier or diluent. The compounds may be administered both orally and parenterally. The pharmaceutical preparations may be in solid form such as capsules, tablets or emulsions. In the treatment of bacterial infections in man, the compounds of this invention may be administered parenterally in an amount of from about 5 to 200 mg./kg./day in divided dosage, e.g. 3 to 4 times a day. They are administered in dosage units containing e.g. 125, 250 or 500 mg. of active ingredient with suitable physiologically acceptacle carriers or excipients.

The following illustrates the preparation of starting materials used in the production of the novel compounds of the invention.

STARTING MATERIALS

Preparation of D (−)2-amino-2-(4-acetoxyphenyl)acetic acid

Method A (in acetic acid as solvent)

203.5 g (1 Mole) of 2-D-(−)-p-hydroxyphenylglycine chloride 800 ml of acetic acid and 314 g (4 Moles) of acetyl chloride are stirred 48 hours at room temperature. The solid is collected, washed three times with acetone (3 × 250 ml) and twice with ethanol (2 × 250 ml) and dried at 40°. Yield 210 g (85.4%). This hydrochloride is dissolved in 3.0 l of water; the solution is cooled to +5 to 10° C and the pH adjusted to 4.5 with 20% NH$_4$OH. The suspension is stirred 1 hour at 5° C and the solid collected, washed twice with water and twice with acetone, and dried at 40° C. Yield 133 g (64% from 2-D-(−)-p-hydroxyphenylglycine). αD (1% HCl N/10) = −104.5

Method B (in methylene chloride)

4.07 g (0.02 Mole) of 2-D-(−)-p-hydroxyphenylglycine hydrochloride, 30 ml of methylene chloride and 6.28 g (0.08 Mole) of acetyl chloride are stirred 48 hours at room temperature. The solid is collected, washed twice with acetone and twice with ethanol. Yield 4.17 g (84.5%). Anal. cl = 14.8% (calculated 14.4%)

Method C (in trifluoroacetic acid)

1.67 g (0.01 Mole) of 2-D-(−)-p-hydroxyphenylglycine is added with stirring, to 10 ml of trifluoroacetic acid at room temperature. After dissolution, 1.57 g (0.02 Mole) of acetyl chloride is added. After a slightly exothermic reaction, a solid appears. The suspension is stirred 1½ hours at room temperature and the trifluoroacetic acid is removed in vacuum. The remaining solid is collected, washed with methylene chloride and with ethanol. The D-(−)-2-amino-2-(4-acetoxyphenyl)acetic acid is identical to that prepared by methods A or B. Yield: 1.9 g (75%)

Preparation of D (−)2-amino-2-(4-acetoxyphenyl)acetyl chloride hydrochloride 83.6 g. (0.40 mole) of D(−)2-amino-2-(4-acetoxyphenyl)-acetic acid and 1.25 l. of anhydrous methylene chloride are cooled to −5° C. with stirring. Then 152 g. of phosphorous pentachloride are slowly added followed by 4 ml. of dimethyl formamide. The mixture is stirred 4 hours at 0° C. The solid is collected, washed with anhydrous methylene chloride and vacuum dried at room temperature. Yield: 61 g. (57.5%).

Anal. Total chlorine = 27.2% (Theory 26.9%)

DESCRIPTION OF THE PREFERRED EMBODIMENTS

All temperatures are in degrees Centigrade. 7-Aminocephalosporanic acid is abbreviated as 7-ACA and 7-aminodesacetoxycephalosporanic acid as 7-ADCA.

7-D-2-Amino-2-(4-acetoxyphenyl)acetamido-desacetoxycephalosporanic Acid-(p-Acetoxycephalexin) — RN 1394

15.27 g (0.0714 Mole) of 7-ADCA are stirred in 500 ml. of anhydrous methylene chloride; 120 ml. of methylene chloride are distilled off and 11.8 ml. of hexamethyldisilazane are added. The mixture is stirred and refluxed 20 hours (after about 10–15 hours all the 7-ADCA has gone into solution). The above solution is cooled to 0° C. and 120 ml. of methylene chloride is added followed by the addition of 9.5 ml. of dimethylaniline and 7 ml. of a solution of dimethylaniline hydrochloride in methylene chloride (30%). Then 20 g. (0.0756 Mole) of D-(—)-2-amino-2-(4-acetoxyphenyl)acetyl chloride hydrochloride are added in small portions (about 1½ hours) at 0° C. The mixture is stirred 30 minutes at +10° C. and 4 hours at +20° C. and allowed to stand overnight at +5° C. Then 5 ml. of methanol followed by 240 ml. of water are added. The pH is adjusted at 2.5 with triethylamine and the mixture is filtered through a diatomaceous earth (Celite) pad; then the pH is checked and the aqueous phase is separated, washed twice (2 × 150 ml.) with methylene chloride and treated with charcoal.

The solution is adjusted to pH 4.5 and vacuum concentrated to a volume of about 150 ml. The suspension is allowed to stand overnight at +5° C and the solid collected and washed with water and acetone and dried at 40° C.

Yield: 15.1 g (about 50% of 75–80% pure material)
$\alpha D$ (1% $H_2O$) = +107

14 g of this crude material is suspended in 30 ml of water (pH = 3.2); hydrochloric acid (36%) is added to pH 1.3 and the resulting solution is charcoal treated and filtered through a Celite pad and adjusted to pH 4–4.5 with stirring. After 2 hours at 0° to +5° C. the RN 1394 is collected, washed with water and acetone and dried at 40° C.

Yield: 7 g.
$\alpha D$(1% $H_2O$) = +133.

The infrared and nuclear magnetic resonance spectra are consistent with the desired product.

Biological Data

Table I shows comparative MIC data for BL-S 578-4 (p-hydroxy analog of cephalexin) and p-acetoxycephalexin (RN 1394). Minimal inhibitory concentrations were determined by the 2-fold broth dilution method utilizing equimolar concentrations of each compound.

Table I

| Nutrient Broth Organisms | | MIC (µg/ml) BL-S 578-4 p-hydroxy-cephalexin | p-acetoxy-cephalexin RN 1394 |
| --- | --- | --- | --- |
| D. pneumoniae* (10–3)** | A9585 | 0.6 | .08 |
| Str. pyogenes* (10–3)** | A9604 | .08 | .08 |
| S. aureus Smith (10–4) | A9537 | 1.3 | 0.6 |
| S. aureus +50% serum (10–4) | A9537 | 1.3 | 0.6 |
| S. aureus BX1633 (10–3) | A9606 | 2 | 1 |
| S. aureus BX1633 (10–2) | A9606 | 2 | 2 |
| S. aureus Meth-Res (10–3) | A15097 | 16 | 32 |
| Sal. enteritidis (10–4) | A9531 | 8 | 8 |
| E. coli Juhl (10–4) | A15119 | 16 | 32 |
| E. coli (10–4) | A9675 | 32 | 63 |
| K. pneumoniae (10–4) | A9977 | 16 | 16 |
| K. pneumoniae (10–4) | A15130 | 32 | 32 |
| Pr. mirabilis (10–4) | A9900 | 8 | 8 |
| Pr. morganii (10–4) | A15153 | >125 | >125 |
| Ps. aeruginosa (10–4) | A9848A | >125 | >125 |
| Ser. marcescens (10–4) | A20019 | >125 | >125 |
| Ent. cloacae (10–4) | A9656 | >125 | >125 |
| Ent. cloacae (10–4) | A9657 | 16 | 8 |
| cloacae Ent. (10–4) | A9659 | >125 | >125 |

*45% AAB ± 5% serum ±50% NB
**Dilution of overnight broth culture

In addition to the above, the compounds of the instant invention are also valuable as intermediates for the preparation of other pharmaceutically active compounds. For example, the instant α-amino-α-(p-acyloxyphenyl)acetamido- desacetoxycephalosporanic acids may be converted to the corresponding p-hydroxy compounds which are known to be potent antibacterial agents useful in the treatment of infectious diseases in poultry and animals, including man, caused by many Gram-positive and Gram-negative bacteria. The conversion can be carried out chemically by simple acid or base hydrolysis in an aqueous medium in most circumstances.

We have found that 7-D-α-amino-α-(p-acetoxyphenyl)-acetamido-desacetoxycephalosporanic acid, although stable in normal saline, is hydrolyzed enzymatically to the known and potent 7-D-α-amino-α-(p-hydroxyphenyl)acetamido-desacetoxycephalosporanic acid.

Accordingly, the present invention also provides for a novel process for preparing 7-D-α-amino-α-(p-hydroxyphenyl)acetamido-desacetoxycephalosporanic acid, hydrate or a pharmaceutically acceptable salt thereof, which process comprises treating in an aqueous solution 7-D-α-amino-α-(p-acetoxyphenyl)acetamido-desacetoxycephalosporanic acid with an esterase at a pH between about 5.0 and about 7.5; isolating the product by methods known per se, and, if desired, converting by methods known per se the product in the form of the free acid or hydrate to the corresponding pharmaceutically acceptable salt thereof.

A preferred embodiment is the preparation of 7-D-α-amino-α-(p-hydroxyphenyl)acetamido-desacetoxycephalosporanic acid, hydrate or a pharmaceutically acceptable salt which process comprises treating in aqueous solution 7-D-α-amino-α-(p-acetoxyphenyl)acetamido-desacetoxycephalosporanic acid with an esterase selected from human serum, animal serum, citrus esterase, wheat bran, wheat germ, and bacillus subtilis at a pH between about 5.0 and about 7.5 and at a concentration of about 5 to about 10 mg./ml. of esterase per total volume of the aqueous solution; isolating the product by methods known per se, and, if desired, converting the product in the form of free acid or hydrate to the corresponding pharmaceutically acceptable salt thereof.

A commercially preferred embodiment of the present invention is the preparation of 7-D-α-amino-α-(p- hydroxyphenyl)acetamido-desacetoxycephalosporanic acid, hydrates or pharmaceutically acceptable salts thereof, which process comprises:

treating in an aqueous solution 7-D-α-amino-α-(p-acetoxyphenyl)acetamido-cephalosporanic acid with an esterase selected from citrus esterase, wheat bran, and wheat germ at a pH between about 5.0 and about 7.5 and at a concentration of about 5 to about 10 mg./ml. of esterase per total volume of the aqueous solution; and isolating the product by methods known per se, and, if desired, converting the product in the form of the free acid or hydrate to the corresponding pharmaceutically acceptable salt thereof.

Of special commercial interest is the process for preparing 7-D-α-amino-α-(p-hydroxyphenylacetamido-desacetoxy-cephalosporanic acid, hydrate or pharmaceutically acceptable salt thereof comprising:

treating in an aqueous solution 7-D-α-amino-α-(p-acetoxyphenyl)acetamido-desacetoxycephalosporanic acid with the commercially available esterase, coarse wheat bran, at a pH between 5.5 and 6.0 or optionally in the presence of a buffer at a pH of 7.0 at a concentration of about 10 mg./ml. of esterase per total volume of solution; and isolating the product by methods known per se, and, if desired, converting the product in the form of a free acid or hydrate to the corresponding pharmaceutically acceptable salt thereof.

The 7-D-α-amino-α-(p-hydroxyphenyl)acetamido-desacetoxycephalosporanic acid prepared by the instant invention is known to be a potent antibacterial agent useful in the treatment of infectious diseases in poultry and animals, including man, caused by many Gram-positive and Gram-negative bacteria.

Solutions of 0.5 mg./ml. of 7-D-α-amino-α-(p-acetoxyphenyl)acetamido-desacetoxycephalosporanic acid (p-acetoxycephalexin) in normal saline and in human serum were prepared. Standard solutions of 0.5 mg./ml. of 7-D-α-amino-α-(p-hydroxyphenyl)acetamido-desacetoxycephalosporanic acid (p-hyroxycephalexin) were also prepared in both normal saline and human serum.

All the above solutions were incubated at 37° C. with shaking and sampled for chromatography at time intervals of 0, 2, 4, 8 and 24 hours. The solutions, approximately 5 microliters per strip, were spotted on Whatman No. 1 half-inch strips which were dried and developed in a solvent system containing 80 parts butylacetate; 15 parts n-butanol; 40 parts acetic acid; and 24 parts water. The strips were then bioautographed on plates seeded with *bacillus subtilis* at a pH of 6.0.

The biochromatograms indicated that p-acetoxycephalexin is quickly hydrolyzed to the p-hydroxy form in human serum but appears stable in normal saline.

We claim:

1. The compound 7-D-α-amino-α-(p-acetoxyphenyl)acetamido-3-methyl-3-cephem-4-carboxylic acid when substantially free of the L-isomer.

* * * * *